(12) United States Patent
Edwards et al.

(10) Patent No.: US 9,164,033 B2
(45) Date of Patent: Oct. 20, 2015

(54) INVESTIGATION OF PHYSICAL PROPERTIES OF AN OBJECT

(75) Inventors: David John Edwards, Oxford (GB); Christopher John Stevens, Oxford (GB)

(73) Assignee: ISIS INNOVATION LIMITED, Oxford (GB)

( * ) Notice: Subject to any disclaimer, the term of this patent is extended or adjusted under 35 U.S.C. 154(b) by 753 days.

(21) Appl. No.: 13/122,791

(22) PCT Filed: Oct. 12, 2009

(86) PCT No.: PCT/GB2009/002436
§ 371 (c)(1), (2), (4) Date: May 9, 2011

(87) PCT Pub. No.: WO2010/043851
PCT Pub. Date: Apr. 22, 2010

(65) Prior Publication Data
US 2011/0237956 A1    Sep. 29, 2011

(30) Foreign Application Priority Data

Oct. 13, 2008    (GB) .................................. 0818775.9

(51) Int. Cl.
*A61B 6/00* (2006.01)
*G01N 21/47* (2006.01)
(Continued)

(52) U.S. Cl.
CPC .......... *G01N 21/4795* (2013.01); *A61B 5/0048* (2013.01); *A61B 5/05* (2013.01);
(Continued)

(58) Field of Classification Search
CPC ...... A61B 5/0048; A61B 5/05; A61B 5/0507; A61B 8/08; A61B 8/0825; A61B 8/488; G01N 2021/1706; G01N 21/4795; G01N 22/00; G01S 15/899
See application file for complete search history.

(56) References Cited

U.S. PATENT DOCUMENTS 5,099,848 A    3/1992   Parker et al.
5,174,298 A   12/1992   Dolfi et al.
(Continued)

FOREIGN PATENT DOCUMENTS

EP    0832599 A1    4/1998
EP    1039313 A1    9/2000
(Continued)

OTHER PUBLICATIONS

Lawrence & Sarabandi, "Electromagnetic Scattering from Vibrating Penetrable Objects Using a General Class of Time-Varying Sheet Boundary Conditions" IEEE Transactions on Antennas and Propagation, vol. 54, No. 7, pp. 2054-2061, Jul. 2006.
(Continued)

*Primary Examiner* — Ruth S Smith
(74) *Attorney, Agent, or Firm* — Harness, Dickey & Pierce, P.L.C.

(57) ABSTRACT

An imaging system for an object such as human or animal tissue uses scattering of an illuminating electromagnetic wave by acoustic vibrations to generate a scattered electromagnetic wave including Doppler components shifted from the frequency of the illuminating electromagnetic wave by frequencies of the acoustic vibration and multiples thereof. An acoustic transducer apparatus applies acoustic vibrations localized in two or three dimensions in a plurality of regions. A transmitter simultaneously illuminates the object with an illuminating electromagnetic wave that has a frequency in the range from 100 MHz to 100 GHz, the vibration direction of the acoustic vibration having a component parallel to the propagation direction of the illuminating electromagnetic wave. A receiver receives the scattered electromagnetic wave. A signal processing apparatus derives characteristics of the Doppler components, and stores image data representing the derived characteristic.

32 Claims, 3 Drawing Sheets

(51) Int. Cl.

| | | |
|---|---|---|
| *A61B 5/00* | (2006.01) | |
| *A61B 5/05* | (2006.01) | |
| *G01N 22/00* | (2006.01) | |
| *A61B 8/08* | (2006.01) | |
| *G01N 21/17* | (2006.01) | |
| *G01S 15/89* | (2006.01) | |

(52) U.S. Cl.
CPC .............. *A61B 5/0507* (2013.01); *G01N 22/00* (2013.01); *A61B 8/08* (2013.01); *A61B 8/0825* (2013.01); *A61B 8/488* (2013.01); *G01N 2021/1706* (2013.01); *G01S 15/899* (2013.01)

(56) References Cited

U.S. PATENT DOCUMENTS

| | | | |
|---|---|---|---|
| 5,212,667 | A | 5/1993 | Tomlinson, Jr. et al. |
| 5,293,873 | A | 3/1994 | Fang |
| 6,002,958 | A | 12/1999 | Godik |
| 6,245,015 | B1 | 6/2001 | Pattanayak |
| 6,645,144 | B1 | 11/2003 | Wen et al. |
| 6,738,653 | B1 | 5/2004 | Sfez et al. |
| 6,957,099 | B1 | 10/2005 | Arnone et al. |
| 6,974,415 | B2 | 12/2005 | Cerwin et al. |
| 2005/0100866 | A1 | 5/2005 | Arnone et al. |
| 2005/0256403 | A1 | 11/2005 | Fomitchov |
| 2006/0122475 | A1 | 6/2006 | Balberg et al. |
| 2007/0015992 | A1 | 1/2007 | Filkins et al. |
| 2007/0038095 | A1 | 2/2007 | Greenleaf et al. |
| 2007/0233056 | A1 | 10/2007 | Yun |
| 2008/0161674 | A1 | 7/2008 | Monro |
| 2009/0264722 | A1 | 10/2009 | Metzger et al. |
| 2009/0281422 | A1* | 11/2009 | Salama et al. ............... 600/430 |
| 2009/0316854 | A1 | 12/2009 | Ismail et al. |
| 2010/0036240 | A1 | 2/2010 | Ismail et al. |

FOREIGN PATENT DOCUMENTS

| | | | |
|---|---|---|---|
| EP | 1810610 | A1 | 7/2007 |
| EP | 2016891 | A1 | 1/2009 |
| EP | 2378272 | A1 | 10/2011 |
| GB | 1326612 | A | 8/1973 |
| JP | 63246627 | A | 10/1988 |
| JP | 2000298776 | A | 10/2000 |
| WO | WO-9533987 | A1 | 12/1995 |
| WO | WO-9854600 | A1 | 12/1998 |
| WO | WO-0165240 | A1 | 9/2001 |
| WO | WO-0208740 | A2 | 1/2002 |
| WO | WO-2005025399 | A2 | 3/2005 |
| WO | WO-2006097910 | A1 | 9/2006 |
| WO | WO-2008040771 | A2 | 4/2008 |
| WO | WO-2010043851 | A1 | 4/2010 |

OTHER PUBLICATIONS

Schmitt & Sengupta, "On the Reflection of Electromagnetic Waves from a Medium Excited by Acoustic Waves", Journal of Applied Physics, vol. 31, No. 2, pp. 439-440, Feb. 1960.
Schmitt & Wu, "Electromagnetic Reflection from Sound Waves", The Journal of the Acoustical Society of America, vol. 32, No. 12, pp. 1660-1667, Dec. 1960.
Lawrence & Sarabandi, "Electromagnetic Scattering from Vibrating Metallic Objects Using Time-Varying Generalized Impedance Boundary Conditions", IEEE Transactions on Antennas and Propagation, vol. 2, pp. 782-785, Jan. 2002.
Buerkle & Sarabandi, "Analysis of Acousto-Electromagnetic Scattering from a Dielectric Cylinder Using the Finite-Difference Time-Domain Method" Proceeding: IEEE Interaction Antennas and Propagation & URSI Symposium, Albuquerque, NM, pp. 3279-3281, Jul. 9-14, 2006.
Chen, "Analysis of Radar Micro-Doppler Signature With Time-Frequency Transform", Proceedings of the 10th IEEE Workshop on Statistical Signal and Array Processing, pp. 463-466, 2000.
Braunreiter et al. "On the Use of Space-Time Adaptive Processing and Time-Frequency Data Representations for Detection of Near-Stationary Targets in Monostatic Clutter", Proc. 10th IEEE Workshop on Statistical Signal and Array Processing, pp. 472-475, 2000.
Chen & Lipps, "Time-Frequency Signatures of Micro-Doppler Phenomenon for Feature Extraction", Proc of SPIE Conference on Wavelet Applications VII, vol. 4056, Orlando, FL, USA, pp. 220-226, Apr. 26, 2000.
Greneker et al., "Extraction of micro-Doppler from vehicle targets at X-band frequencies", Proc of SPIE Conference on Radar Sensor Technology VI, vol. 4374, pp. 1-9, 2001.
Japanese Office Action dated Jun. 11, 2013. Translation provided by J A Kemp.
International Search Report and Written Opinion for GB/2009/002436, mailed Feb. 3, 2010.
Ian Poole. "PLL FM demodulator/detector." Adrio Communications Ltd. Jun. 13, 2011.
Géza Kolumbán. "Phase-Locked Loops." The Encylopedia of FR and Microwave Engineering, vol. 4. Jan. 1, 2005. pp. 3735-3767.
International Search Report regarding Application No. PCT/GB2012/052310, mailed Jan. 1, 2013.

\* cited by examiner

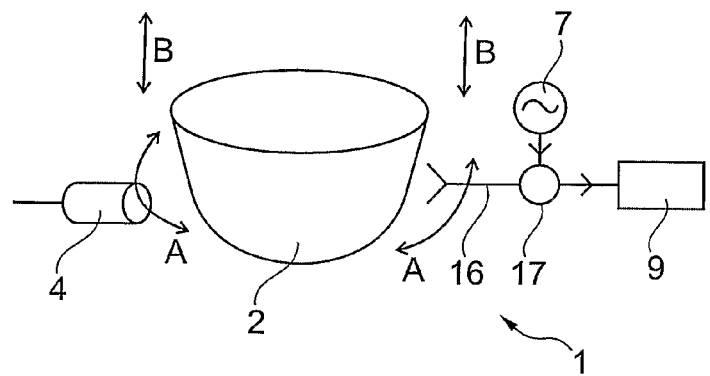
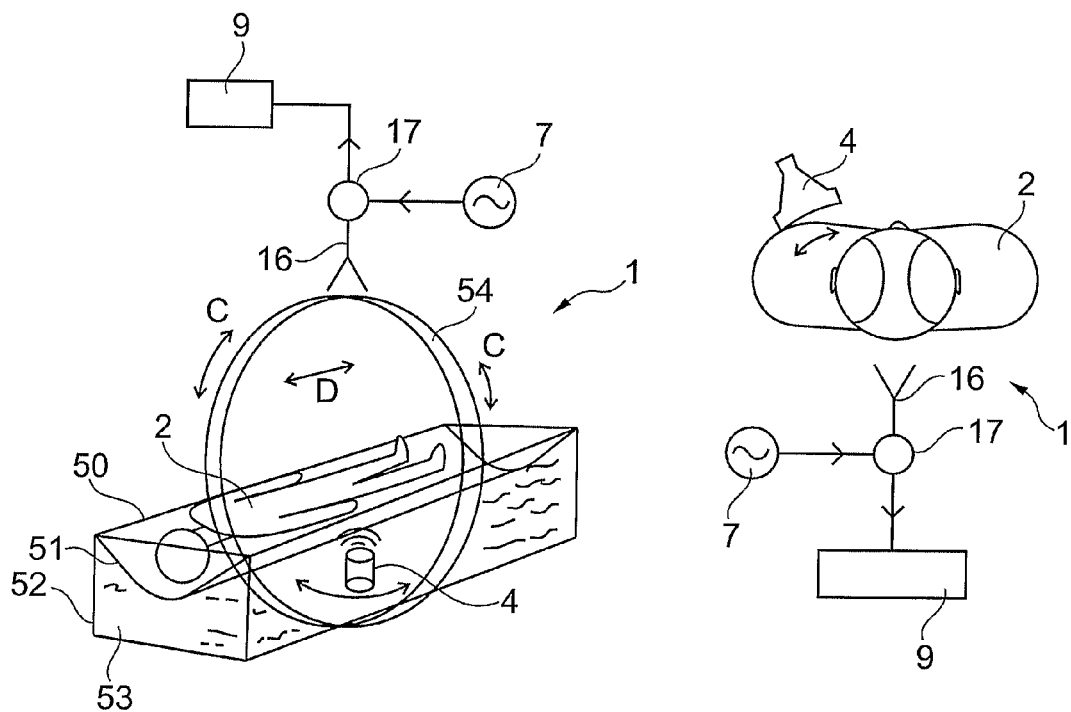
Fig. 7
Fig. 8
Fig. 9

INVESTIGATION OF PHYSICAL PROPERTIES OF AN OBJECT

CROSS-REFERENCE TO RELATED APPLICATIONS

This application is a 371 U.S. National Stage of International Application No. PCT/GB2009/002436, filed Oct. 12, 2009. This application claims priority to British patent application No. 0818775.9, filed with the Intellectual Property Office on Oct. 13, 2008, which is herein incorporated by reference in its entirety.

The present invention relates to the investigation of physical properties of an object. It has application in the field of imaging although not exclusively.

Various methods for investigating the physical properties of an object are known. For example there are a wide range of imaging techniques which produce an image of an object representing its physical properties. For example in the field of medical imaging, established and widely used imaging methods include x-ray radiography, computed tomography (CT), ultrasound imaging, magnetic resonance imaging (MRI), positron emission tomography (PET).

Different imaging methods are based on different physical phenomena. For example in x-ray radiography and computed tomography (CT) x-rays interact with the object, in ultrasound imaging ultrasound interacts with the object, and so on. As a result different imaging techniques produce images of different physical characteristics of the object being imaged. Thus different imaging techniques have different advantages and limitations. By way of example, comparing both of the common medical imaging methods of ultrasound imaging and MRI provide relatively high resolution images, but ultrasound imaging provides images of acoustic or mechanical properties whereas MRI provides images of electromagnetic properties. Thus MRI is more useful for imaging some objects, but conversely suffers from the problem of requiring powerful magnets.

Similarly, there are a range of spectroscopic techniques based on different physical phenomena. Such spectroscopic techniques do not necessarily produce an image but provide data in respect of a range of frequencies or wavelengths, for example of electromagnetic radiation.

Due to the different physical phenomena on which they are based, such different imaging techniques and different spectroscopic techniques have different applications, depending on the nature of the features of interest in the object.

The present invention is concerned with a technique for investigating the physical properties of an object which is different from such established techniques.

According to a first aspect of the present invention, there is provided a method of investigating physical properties of an object, comprising:

applying to the object acoustic vibration localized in two or three dimensions in a region in the object;

simultaneously illuminating the object with an illuminating electromagnetic wave that has a frequency in a range extending down from 30 THz, the vibration direction of the acoustic vibration having a component parallel to the propagation direction of the illuminating electromagnetic wave so that the acoustic vibration of the object in the region generates a scattered electromagnetic wave including Doppler components shifted from the frequency of the illuminating electromagnetic wave by frequencies of the acoustic vibration and multiples thereof; and receiving the scattered electromagnetic wave generated in the region, and deriving from the received, scattered electromagnetic wave data representing at least one characteristic of the Doppler components.

According to a further aspect of the present invention, there is provided a system implementing a similar method.

Thus the present invention provides for investigation of physical properties of an object based on the physical phenomenon of an acoustic vibration of the object scattering and modulating an electromagnetic wave that has a frequency in a range extending down from 30 THz illuminating the object, that is a radio wave in the Terahertz band or below. The present invention is advantageously applied to an object that is human or animal tissue, for example in the field of medical imaging. However, the present invention is not restricted to that field and may be applied to a range of objects in other fields.

By means of the vibration direction of the acoustic vibration having a component parallel to the propagation direction of the illuminating electromagnetic wave, the scattered electromagnetic wave includes Doppler components shifted from the frequency of the illuminating electromagnetic wave by frequencies of the acoustic vibration and multiples thereof. Characteristics of such Doppler components are detected. The detected characteristics are dependent on the mechanical response of the object in that region to the applied acoustic vibration and on the electromagnetic properties of the object in that region which cause an interaction with the illuminating electromagnetic wave. Thus the detected characteristics provide information on electromagnetic properties similar to MRI imaging but without requiring magnets.

The present invention may be applied to provide imaging of the object. In this case the acoustic vibration is applied localized in a plurality of regions and the scattered electromagnetic wave generated in each of the plurality of regions is received and used to derive data representing at least one characteristic of the Doppler components in respect of each region as image data.

Thus, there is simultaneously applied localized acoustic vibration and an electromagnetic wave, and, as the acoustic vibration is localized in two or three dimensions in a region in the object, any detected Doppler components (being shifted from the frequency of the illuminating electromagnetic wave by frequencies of the acoustic vibration or multiples thereof) are known to have been generated by the interaction in the region of the acoustic vibration. In this way, it is possible to generate image data for a plurality of regions and thus build up an image representing information on the physical properties of the object. In the case that the acoustic vibration is localized in two dimensions, then the regions extend in the third direction and thus the image is a two dimensional image (or shadow image). In the case that the acoustic vibration is localized in three dimensions, then the regions are limited in extent in that third direction and a three-dimensional image may be derived.

The acoustic vibration may be applied localized at the plurality of regions sequentially. In this case, the acoustic vibration may have the same frequency which simplifies implementation of the method but is not essential.

Alternatively, the acoustic vibration may be applied localized in the plurality of regions simultaneously but with different frequencies in each region. In this case, the electromagnetic waves scattered from each region have different frequencies, allowing the data representing at least one characteristic of the Doppler components to be separately derived in respect of each region.

The localization may be achieved in a similar manner to known ultrasound imaging techniques. For example, to apply acoustic vibration localized in two dimensions, the acoustic vibration may be applied as a beam, or, to apply acoustic vibration localized in three dimensions, the acoustic vibration may be applied as a spot continuously localized in three dimensions or as a pulsed beam localized in space in two dimensions and localized along the propagation direction at different times as the acoustic vibration propagates. This means that the resolution of the imaging is similar to that achieved by ultrasound imaging, being limited by the localization achievable on the basis of the wavelength of the acoustic vibration.

The present invention may also be used applying the acoustic vibration to just a single region without providing imaging of the object. Nonetheless, the information on the physical properties of the object which is derived is useful because it is based on the physical phenomenon described above.

Optionally and with particular advantage in the case of applying the acoustic vibration to just a single region, the method is performed with acoustic vibrations of different frequencies and/or with an illuminating electromagnetic wave of different frequencies. In this way, data representing at least one characteristic of the Doppler components may be obtained in respect of the different frequencies of the acoustic vibrations and/or the illuminating electromagnetic wave. In this case the present invention is implemented as a spectroscopic technique which is useful for some objects because it allows better characterization of the nature of the object.

These properties mean that the imaging of the present invention can provide advantages over the established imaging methods when applied to imaging human or animal tissue, including but not limited to medical imaging.

To allow better understanding, embodiments of the present invention will now be described by way of non-limitative example with reference to the accompanying drawings, in which:

FIG. 1 is a diagram of an imaging system;

FIGS. 2(a) to 2(c) are graphs of the frequency spectrum of the acoustic vibration, the illuminating electromagnetic wave and the scattered electromagnetic wave;

FIG. 7 is a perspective view of the imaging system applied to mammography;

Figure 1:
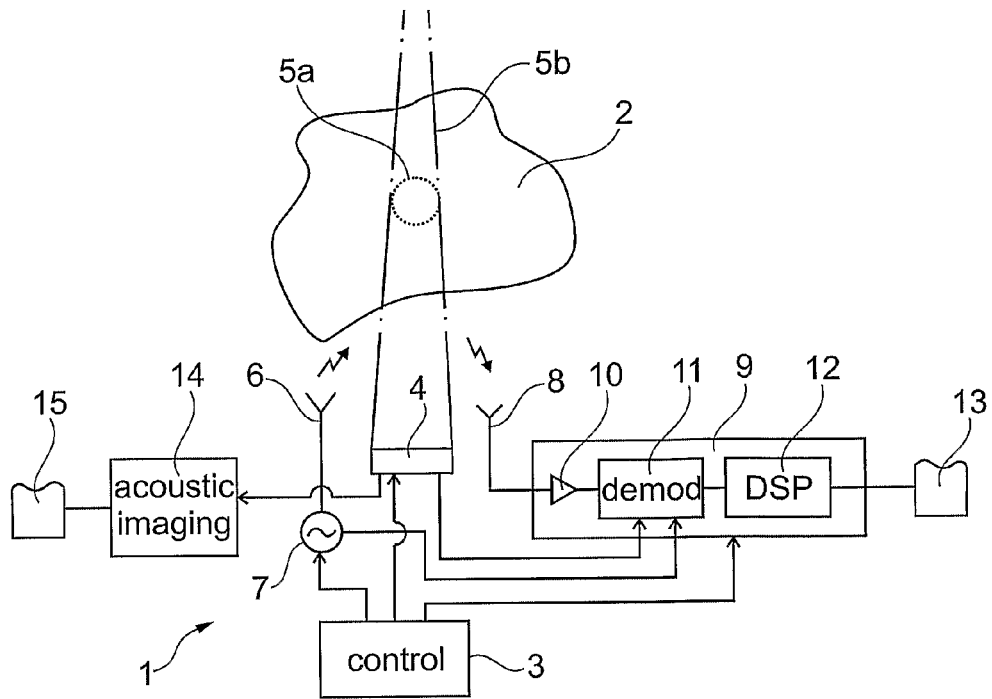

FIG. 8 is a is a perspective view of the imaging system applied as a full body scanner; and FIG. 9 is a perspective view of the imaging system applied using a hand-held acoustic transducer apparatus. There will first be described a system 1 for investigating physical properties of an object 2, as shown in FIG. 1. The object 2 may be human or animal tissue, for example in the field of medical imaging. However, the present invention is not restricted to that field and may be applied to a range of objects in other fields.

The system 1 includes a control unit 3 which controls the other components of the system 1. The control unit 3 may be implemented by a computer apparatus running an appropriate program.

The system 1 includes an acoustic transducer apparatus 4 which operates under the control of the control unit 3. The acoustic transducer apparatus 4 in operation applies acoustic vibration to the object 2. The acoustic vibration is localized in a region 5a or 5b at a given location within the object 2. As alternatives that are both illustrated in FIG. 1, the acoustic vibration may be localized in two dimensions in a region 5a (shown in dashed outline) that is limited in extent perpendicular to the propagation direction of the acoustic vibration but extends along the propagation direction, or may be localized in three dimensions in a region 5a or 5b (shown in dotted outline) that is also limited along the propagation direction. The localization of the acoustic vibration may be achieved using conventional equipment as described in more detail below. When localized in three dimensions, along the direction of propagation of the acoustic wave, the acoustic vibration might be localized only instantaneously as the acoustic wave propagates. In many fields of application such as medical imaging, the acoustic vibration is ultrasonic. In the simplest embodiment, the acoustic vibration is localized at a single location at a given time, that location being scanned over the object 2 so that the acoustic vibration is applied to regions 5a or 5b at a plurality of different regions 5a or 5b successively. Such scanning may be performed by using an acoustic transducer apparatus 4 which has a controllable focus or beam, or alternatively by physically moving the acoustic transducer apparatus 4 with fixed focus or beam, for example using a mechanical translator. The scanning may be carried out in one, two or three dimensions.

In more complicated embodiments, the acoustic vibration is localized in regions 5a or 5b at plural locations simultaneously but in this case the acoustic vibration has different frequencies at different locations, as discussed further below.

For ease of detection, the acoustic vibration is predominantly of a single frequency. However, in general the acoustic vibration could include a band of frequencies.

The system 1 also includes a transmitter arrangement comprising a transmitter antenna 6 connected to a radio frequency source 7 controlled by the control unit 3. The transmitter arrangement in operation illuminates the object 2 with an illuminating electromagnetic wave having a radio frequency and having a sufficiently broad beam to cover the entire volume of the object 2 under investigation, ideally uniformly. The illuminating electromagnetic wave is desirably a continuous wave rather than a pulse. In this case the illuminating electromagnetic wave has a constant amplitude and frequency, at least over the period for which the interaction with the acoustic wave is monitored by receiving the scattered Doppler components.

For ease of detection, the illuminating electromagnetic wave is predominantly of a single frequency, but in general the illuminating electromagnetic wave could include a band of frequencies. The frequency of the illuminating electromagnetic wave is greater than the frequency of the acoustic vibration, preferably by at least an order of magnitude.

The illuminating electromagnetic wave is scattered by the object 2. Within the region 5a or 5b, there is an interaction between the acoustically vibrating object 2 and the illuminating electromagnetic wave which causes the acoustic vibration of the object 2 in the region 5a or 5b to modulate the scattered electromagnetic wave. In particular, the scattered electromagnetic wave which is generated includes a component at the frequency of the illuminating electromagnetic wave and Doppler components at frequencies shifted from the frequency of the illuminating electromagnetic wave by frequencies of the acoustic vibration and multiples thereof.

Figure 2A:
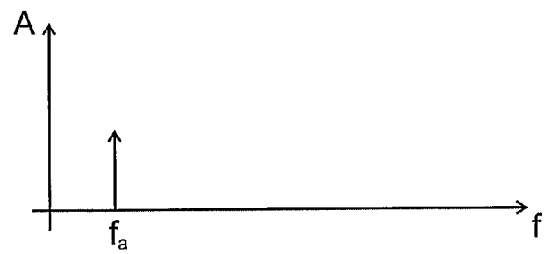
Figure 2B:
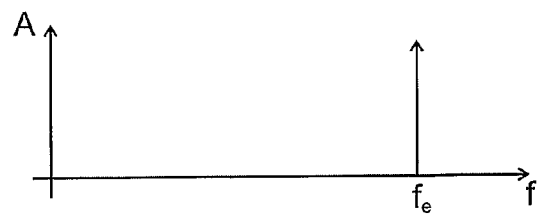
Figure 2C:
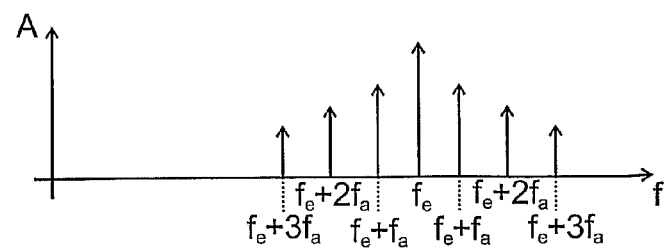

This is illustrated graphically in FIGS. 2(a) to 2(c) which are graphs of the frequency spectrum of the acoustic vibration, the illuminating electromagnetic wave and the scattered electromagnetic wave, respectively. In this case, the acoustic vibration and the illuminating electromagnetic wave each have a single frequency of fa and fe, respectively. The scattered electromagnetic wave has a central component of the frequency fe of the illuminating electromagnetic wave. The scattered electromagnetic wave also has Doppler components (sidebands) at frequencies fe±n.fa, where n is an integer, i.e. shifted from the frequency fe of the illuminating electromagnetic wave by the frequency fa of the acoustic vibration and multiples thereof. Although FIG. 2(c) illustrates an example with three Doppler components on each side, in general there could be any number of Doppler components depending on the physical interaction.

The physical phenomenon behind the generation of the scattered electromagnetic wave including the Doppler components is that boundaries between areas in the object 2 having different electrical properties such as conductivity and dielectric permittivity (or more generally areas where those electrical properties change) scatter the illuminating electrical magnetic wave and that vibration of those boundaries modulates the scattered wave. Thus it may be considered that the central component having the frequency of the illuminating electromagnetic wave corresponds to the scattering of the object 2 when stationary, whereas the Doppler components are generated by the vibration of the object 2.

Indeed this physical phenomenon for the general case of a vibrating object is of itself known, for example as disclosed in Lawrence et al., "Electromagnetic Scattering from Vibrating Penetrable Objects Using a General Class of Time-Varying Sheet Boundary Conditions", IEEE Transactions on Antennas and Propagation, Vol. 54, no. 7, pp. 2054-2061, July 2006. However this document merely considers the electromagnetic wave scattered by metallic and dielectric bodies which are vibrating without considering how the vibration is generated. In contrast in the present invention, the acoustic vibrations are applied localized in a region 5a or 5b, meaning that the any detected Doppler components in the scattered electromagnetic wave are known to have been generated in the region 5a or 5b. On this basis the system 1 uses the Doppler components to provide information about the object 2 at the location of the region 5a or 5b. In particular the detected Doppler components are dependent on the mechanical response (compliance) of the object 2 at the location of the region 5a or 5b to the acoustic vibration and also on the electrical properties of the object 2 at the location of the region 5a or 5b. By applying the acoustic vibration to regions 5a or 5b at different locations it is possible to build up an image of the object 2.

The system 1 also includes a receiver arrangement comprising a receiver antenna 8 connected to signal processing apparatus 9 controlled by the control unit 3. In operation the receiver 8 receives the scattered wave and the signal processing apparatus 9 analyzes it to detect the Doppler components and derive to the phase and amplitude of the Doppler components, or in general other characteristics of the Doppler components.

In FIG. 1, the acoustic transducer apparatus 4 and the transmitter antenna 6 are shown alongside each other so that the propagation direction of the acoustic vibration and the electromagnetic wave are the same, but this is not essential and other arrangements are described below. In general, the locations of the acoustic transducer apparatus 4 and the transmitter antenna 6 relative to each other are chosen so that the vibration direction of the acoustic vibration has a component parallel to the propagation direction of the illuminating electromagnetic wave. This is to generate the Doppler scattering.

The magnitude of the scattered Doppler components is maximized by the vibration direction of the acoustic vibration being parallel to the propagation direction of the illuminating electromagnetic wave. The vibration direction is parallel to the propagation direction of the acoustic vibration, so this corresponds to the acoustic vibration and the illuminating electromagnetic wave having parallel or antiparallel directions. This is because, the mechanical movement of the region 5a or 5b resolved along the propagation direction of the illuminating electromagnetic wave is greatest in this direction, ignoring secondary motions which may be induced in other directions due to mechanical distortion of bulk material. If there is an angle α between the direction of the acoustic vibration and the propagation direction of the illuminating electromagnetic wave, then the velocity of the acoustic vibration resolved along the propagation direction of the illuminating electromagnetic wave is reduced, scaling with cos(a). This has the effect that the magnitude of the scattered Doppler components is similarly reduced, scaling with cos(a). Effectively this means that the vibration direction of the acoustic vibration should not be perpendicular to the propagation direction of the illuminating electromagnetic wave, and is preferably parallel, although the Doppler components may still be observed with higher angles α.

The acoustic transducer apparatus 4 and the transmitter antenna 6 may be located adjacent one another to set the direction of the acoustic vibration parallel to the propagation direction of the illuminating electromagnetic wave. An exactly parallel condition is limited by the constraints imposed by the physical bulk of the acoustic transducer apparatus 4 and the transmitter antenna 6 but they may be arranged sufficiently close to be parallel for the practical purpose of maximising the Doppler scattering. Alternatively, the transmitter antenna 6 may be arranged on the opposite side of the object 2 from the acoustic transducer apparatus 4.

In general, the receiver antenna 8 may be located at any angle relative to the propagation direction of the electromagnetic wave and the vibration direction of the acoustic vibration. This is because the scattered Doppler components can in principle be scattered in any direction. The direction of scattering depends on the physical properties of the object 2 in the region 5a or 5b.

Advantageously, the scattered electromagnetic wave is received along a line parallel or antiparallel to the propagation direction of the illuminating electromagnetic wave because the scattering is typically strong in these directions. Reception along a line antiparallel to the propagation direction of the illuminating electromagnetic wave may be achieved by the transmitter antenna 6 and the receiver antenna 8 being located close together (subject to the constraints imposed by their physical bulk) or being replaced by a common antenna connected to appropriate circuitry (such as a directional coupler) to isolate the frequency source 7 from circuitry handling the detected Doppler components.

However, the scattered electromagnetic wave may be received in other directions. Advantageously, the scattered electromagnetic wave is received in plural directions. This can provide additional information on the nature of object 2 in the region 5a or 5b because the direction of scattering depends on the physical properties of the object 2 which causes the scattering.

The signal processing apparatus 9 includes an amplifier 10, a frequency-modulation (FM) demodulator 11 and a digital signal processor 12.

The amplifier 10 receives and amplifies the signal received by the receiver 8. The amplified signal output by the amplifier 10 is supplied to the FM demodulator 11 which is arranged to derive the phase and amplitude of the Doppler components of the scattered wave. As the modulation of the illuminating electromagnetic wave by the vibration of the region 5a or 5b is primarily frequency-modulation, the FM demodulator 11 may employ conventional FM techniques to derive characteristics of the Doppler components such as phase and amplitude. To facilitate the FM demodulation, the FM demodulator 11 is provided with the signal of the illuminating electromagnetic wave from the frequency source 7 and with the signal of the acoustic wave from the acoustic transducer apparatus 4.

In the case that acoustic vibration in a region 5a or 5b at a given location is at a single frequency, the FM demodulator 11 may include a coherent detector arranged to detect the frequency of the acoustic wave in the Doppler components.

The amplifier 10 and FM demodulator 11 are typically formed by analog circuits, but digital circuits could alternatively be used.

The phase and amplitude of the Doppler components derived by the FM demodulator 11 are supplied to the digital signal processor 12 which processes those characteristics of the Doppler components. As the FM demodulator detects characteristics of the Doppler components which are at a frequency shifted from the frequency of the illuminating electromagnetic wave by frequencies of the acoustic vibration and multiples thereof, those characteristics are known to have been derived from the region 5a or 5b of the object 2 at the current location of the acoustic vibration. The digital signal processor 12 is supplied with information by the control unit 3 identifying the current location of the acoustic vibration. The digital signal processor 12 stores image data 13 representing those characteristics detected in respect of each location as the location is scanned over the object 2. The image data 13 may be stored, displayed and/or output from the signal processing apparatus 9.

The digital signal processor 12 may store only the actually derived values of the phase and amplitude or other characteristics. These vary in dependence on the properties of the object 2 at different locations as discussed above and therefore provide a useful image even without further processing.

Optionally, the digital signal processor 12 may further process the actually derived values of the phase and amplitude or other characteristics, on the basis of a model of the interaction between the acoustic vibration and the illuminating electromagnetic wave, to derive characteristics representing particular physical properties of the object 2 which are also stored as image data 13. Such processing may provide information on properties of the object 2 which are more useful than the phase and amplitude themselves. For example in the case of medical imaging, such processing may be used to characterise metabolite species which have known electromagnetic responses.

The digital signal processor 12 may be implemented by a computer apparatus executing an appropriate program, optionally being the same computer apparatus as used to implement the control unit 3.

As the Doppler components are generated from the interaction caused by the acoustic vibration of the region 5a or 5b, the resolution of the image data 13 is equal to the size of that region 5a or 5b as governed by the degree of localization of the acoustic vibration achieved by the acoustic transducer apparatus 5a or 5b. The resolution is therefore dependent on the wavelength of the acoustic wave in a similar manner to ultrasound imaging. Thus the present imaging technique can achieve similar resolution to that achieved by ultrasound imaging. For example the resolution might be less than a millimeter at very high ultrasound acoustic frequencies (roughly speaking, 1 mm resolution corresponds to a frequency of 1 MHz, 100 µm to 10 MHz, and 1 µm to 100 MHz)

On the other hand, the image contrast mechanism is different from ultrasound imaging being dependent on the physical interaction between the acoustic vibration and the illuminating electromagnetic vibration and providing information on the mechanical response (compliance) of the object 2 to the acoustic vibration and on the electrical properties of the object 2, as discussed above, for example providing similar information to MRI without the requirement for magnets. Thus the present imaging technique can be seen as an alternative to other imaging modalities.

The present imaging technique may be applied to imaging in a range of fields, for example in medical imaging wherein the object 2 is human or animal tissue, by appropriate selection of the frequencies of the acoustic vibration and the illuminating electromagnetic wave.

The illuminating electromagnetic wave is a radio wave having a frequency in a range extending: down from 30 THz, that is in the Terahertz band or below; down from 300 GHz, that is in the EHF (Extremely High Frequency) band or below, corresponding to microwave frequencies or below; or in some fields of application down from 100 GHz. In the case that the object 2 is human or animal tissue, advantageously the range extends down from 100 GHz. This means that the interaction in the object 2 provides information on the electromagnetic properties of the object 2 similar to MRI imaging. For many applications, the range extends down to 100 MHz.

The frequency of the acoustic wave controls the resolution and is therefore chosen to be sufficiently high to achieve the desired resolution having regard to the features of interest in the object 2 being imaged. The frequency of the acoustic wave may be subject to practical constraints similar to those with conventional ultrasound imaging, such as the frequencies achievable by the acoustic transducer apparatus 4, and the penetration of the acoustic waves in the object 2 being imaged. By way of illustration, if the object 2 being imaged is human or animal tissue, for example in the field of medical imaging, the frequency of the acoustic wave might typically be in the range extending down from 10 MHz and/or extending down to 1 GHz. Such frequencies are ultrasonic, although in general acoustic frequencies in the audible range could in principle be used in some fields of application.

The object 2 may have a response which varies at different frequencies. Therefore, the imaging may be performed with acoustic vibrations of different frequencies and/or with an illuminating electromagnetic wave of different frequencies. The different frequencies may be applied at different times by repeating the operation of the system 1 but adjusting the acoustic frequency. Alternatively different frequencies may be applied simultaneously to the same or different regions 5a or 5b. In this way, information may be obtained in respect of the different frequencies of the acoustic vibrations and/or the illuminating electromagnetic wave, so the technique is a spectroscopic technique. This allows better characterization of the nature of the object 2.

The degree of absorption of the illuminating electromagnetic wave in the object 2 increases with its frequency. Thus the frequency of the illuminating electromagnetic wave is chosen to be sufficiently low to provide absorption in the object 2 which is sufficiently low to allow the entire object 2 to be imaged.

The acoustic transducer apparatus 4 and various variations thereof will now be described. As previously mentioned, the acoustic transducer apparatus 4 provides acoustic vibration is localized in a region 5a or 5b at a given time, that is localized in two dimensions in a region 5a that extends in the propagation direction or localized in three dimensions in a region 5b that is limited in the propagation direction. This may be achieved using a conventional apparatus that may provide a controllable focus or a fixed focus.

Figure 3:
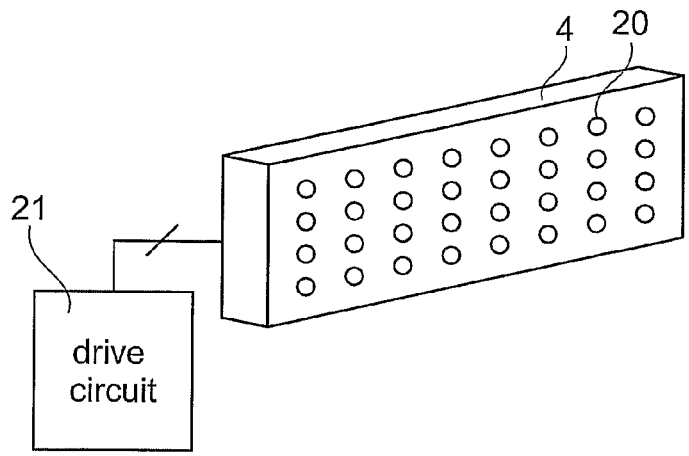
FIG. 3 is a perspective view of an acoustic transducer apparatus of the imaging system.

FIG. 3 shows a possible arrangement in which the acoustic transducer apparatus 4 comprises an array of transducers 20 which provide an electronically controllable focus at a region 5a or 5b. In this case, the acoustic wave output by the array of transducers 20 may be a propagating beam. As known in the field of ultrasound imaging such beam-forming allows a high energy focus is formed at a desired location. In the present method this means that the majority of the scattered electromagnetic wave contains information pertaining to the region 5a or 5b of focus.

To provide localization in two dimensions, the array of transducers 20 may apply the acoustic vibration as a continuous beam, so that the acoustic vibration is localized in space within the propagating beam in the two dimensions perpendicular to the direction of propagation. To provide localization in three dimensions, the array of transducers 20 may still apply the acoustic vibration as a beam that is not continuous so that along the third dimension in the direction of propagation, the acoustic vibration is localized instantaneously as the acoustic wave propagates. The propagating beam may be a pulse which is localized in a single region 5a or 5b at a given time which region 5a or 5b propagates through the object 2 over time. Alternatively the propagating beam may have a varying frequency so that different frequencies of acoustic vibration are localized in different regions 5a or 5b simultaneously. Accordingly, the information supplied by the control unit 3 to the digital signal processor 12 indicates the timing of the propagating beam, thereby identifying the current location of the acoustic vibration.

In the case that the propagating beam has a varying frequency, one option is that the signal processing apparatus 9 is arranged to perform a Fourier Transform, or other transform, of the received scattered signal into the time domain. Due to the different frequencies of acoustic vibration being localized in different regions 5a or 5b simultaneously, such a transform generates the characteristics in respect of each of the different regions 5a or 5b. In this way, a "movie" can be constructed and images as a function of time can be displayed with extremely high temporal/spatial resolution.

Figure 4:
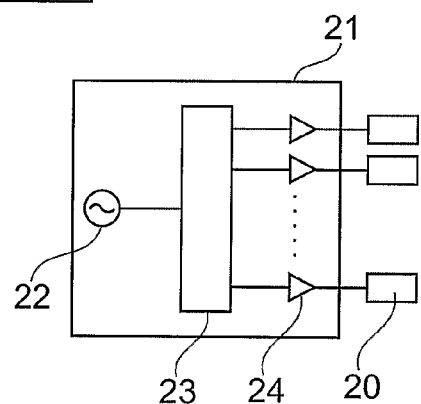
FIG. 4 is diagram of a drive circuit of the acoustic transducer apparatus.

To form the propagating beam, the acoustic transducer apparatus 4 comprises a drive circuit 21 which provides a separate drive signal to each transducer 20 which drive signals vary in amplitude and/or phase and/or delay to form the focus at the desired region 5a or 5b. As shown in FIG. 4, the drive circuit 21 includes a frequency source 22 which provides an oscillating signal of the desired frequency to a beam-former circuit 23. The beamformer circuit 23 derives a signal for each transducer 20 from the oscillating signal by modifying the amplitude and/or phase and/or delay. The beamformer circuit 23 operates under the control of the control unit 3 to provide a focus in a desired region 5a or 5b. The drive circuit 21 also includes amplifiers 24 for amplifying the signal for each transducer 20 output by the beamformer circuit 23 to form the drive signal which is then supplied to the respective transducers 20.

Figure 5:
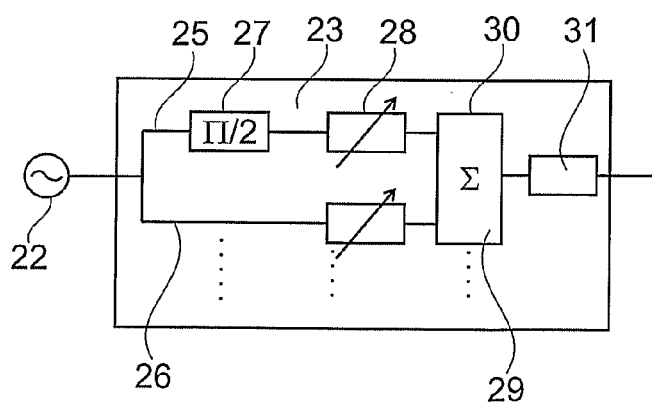
FIG. 5 is a diagram of a beamformer circuit of the drive circuit.

The beamformer circuit 23 may include programmable amplifiers (or attenuators) and/or phase shifters and/or delays to modify the oscillating signal. For example, the beamformer circuit 23 may employ a quadrature arrangement as shown in FIG. 5 in respect of each one of the transducers. This quadrature arrangement comprises an I-channel 25 and a Q-channel 26 each supplied with the oscillating signal from the frequency source 22. The I-channel includes a n/2 phase delay 27 for phase-delaying the oscillating signal so that the signals in the I-channel 25 and Q-channel 26 are in quadrature. The I-channel 25 and Q-channel 26 each include respective attenuators 27 and 28, the outputs of which are supplied to an adder 30 for adding the attenuated quadrature signals. The respective degrees of attenuation provided by each of the attenuators 27 and 28 may be controlled to thereby vary the amplitude and phase of the signal output by the adder 30. This signal output by the adder 30 is optionally provided to a variable delay circuit 31 which may be varied to control the delay of the drive signal.

Figure 6:
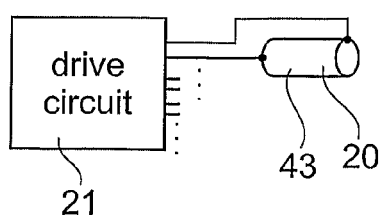
FIG. 6 is a perspective view of a transducer of the acoustic transducer apparatus.

Each transducer 20 may be formed as shown in FIG. 6 by a piece 43 of piezoelectric material (or other electro-active material). The drive signal from the drive circuit 21 is applied across the piece 43 of piezoelectric material which vibrates in response thereto thereby generating an acoustic wave. The piece 43 of piezoelectric material is shown as being cylindrical but may be shaped to direct the generated acoustic wave.

In FIG. 3, the array of transducers 20 is illustrated as a 2D planar array, but in general any arbitrary form of array may alternatively be used, for example a 1D linear or conformal array, a curved or conformal 2D array, a 3D array, or plural arrays on different sides of the object 2.

As an alternative to forming a beam, this acoustic transducer apparatus 4 comprising the array of transducers 20 may apply the acoustic vibration as a spot which is continuously localized in space in three dimensions.

Using this acoustic transducer apparatus 4 comprising an array of transducers 20, the location of the region 5a or 5b at which the acoustic vibration is localized may be scanned over the object 2 under electronic control to derive information on different regions 5a or 5b and thereby build up an image of the object 2.

In the case that the acoustic vibration is localized in two dimensions, then the image is a two dimensional image (or shadow image) whose pixels contain information from the entirety of the region 5a that extend through the object 2 along the propagation direction of the acoustic vibration. In this case, a three dimensional image can be built up by moving the acoustic transducer apparatus 54 and transmitter antenna 6 around the object 2 under examination and taking a series of images with different angles of incidence. Then the series of images may be transformed into a three dimensional image using similar transforms to those conventional for other types of imaging such as computed tomography (CT) scanning.

In the case that the acoustic vibration is localized in three dimensions, then a three-10 dimensional image may be derived by scanning the region 5b in three dimensions.

Such scanning could also be achieved using an acoustic transducer apparatus 4 which has a fixed focus, by physically moving the acoustic transducer apparatus 4.

As previously mentioned, in the simplest embodiment, the acoustic vibration is localized in a single region 5a or 5b at a given time, the acoustic vibration being applied to regions 5a or 5b at a plurality of 15 different locations successively.

In more complicated embodiments, the acoustic vibration is localized in plural regions 5a or 5b at different locations simultaneously. In this case, the acoustic vibration has different frequencies in different regions 5a or 5b.

One option is to use the acoustic transducer apparatus 4 comprising an array of transducers 20 as described above but modified to simultaneously produce plural propagating beams of different frequencies. This may be achieved by replicating the circuitry of the drive circuit 21 described above in respect of each of the different frequencies used. The drive signals in respect of each frequency may be summed and applied to the respective transducers 20.

As the acoustic vibration has different frequencies in different regions 5a or 5b, the scattered 25 electromagnetic wave has Doppler components of different frequencies generated in the different regions 5a or 5b, each having frequencies shifted from the frequency of the illuminating electromagnetic wave by the different frequencies of the acoustic vibration (and multiples thereof). The signal processing apparatus 9 is therefore arranged to detect and derive characteristics of the different Doppler components which are known to have been generated at the different locations of the 30 regions 5a or 5b. This may be achieved by the signal processing apparatus 9 being arranged as described above but replicating the FM demodulator 11 in respect of each of the acoustic frequencies used. In this manner, characteristics of the Doppler components and therefore image data 13 may be simultaneously be derived in respect of plural regions 5a or 5b. Many regions 5a or 5b may be simultaneously imaged in this manner, limited by the ability of the signal processing apparatus 9 to discriminate 35 between Doppler components of different frequencies.

In some arrangements, plural regions 5a or 5b are simultaneously imaged allowing an image to be derived without scanning the regions 5a or 5b. In other arrangements, plural regions 5a or 5b are simultaneously imaged but then the regions 5a or 5b are scanned to image other areas of the object 2. For example, one particular embodiment may employ a plurality of propagating beams arranged in a 1D (or 2D) array to simultaneously image a 1D (or 2D) slice which propagates through the object 2 allowing successive slices to be imaged, thereby building up a 2D (or 3D) image in a similar manner to conventional medical ultrasound imaging as employed for example in obstetric sonography.

Alternatively, the system 1 may be implemented to investigate the properties of the object 2 in a single region 5a or 5b without providing imaging across the object 2. In this case, acoustic vibration is applied to just a single region 5a or 5b. This may be achieved with the system 1 as described above but modifying the control implemented by the control unit 3. Alternatively, the system 1 may be simplified, for example using an acoustic transducer apparatus 4 having a fixed focus because scanning is not required.

When investigating the properties of the object 2 in a single region 5a or 5b, it is particularly advantageous to use acoustic vibrations of different frequencies and/or with an illuminating electromagnetic wave of different frequencies, as described above. The different frequencies may be applied at different times but or simultaneously. In the latter case it is possible to tune the system 1 to simultaneously investigate a wide range of frequencies without needing to use the different frequencies to obtain information on regions 5a or 5b at different locations as is necessary with some imaging implementations.

The size and detailed construction of the system 1 will depend on the field of application. For example for use in medical imaging, the system 1 might be realized as a dedicated device in which the acoustic transducer apparatus 4 is similar to an ultrasound head in a conventional ultrasound imaging apparatus. In this case, the transmitter antenna 6 and receiver antenna 8 might be integrated into the same ultrasound head.

Optionally, the system 1 might additionally incorporate an acoustic system 14 connected to the acoustic transducer apparatus and arranged to receive a reflected acoustic wave from each of the regions 5a or 5b and thereby to derive acoustic image data 15 with derivation of the image data 13 by the signal processing apparatus 9. The acoustic system 14 may be arranged as conventional ultrasound imaging apparatus, thereby allowing the present method to be integrated with conventional ultrasound imaging. The acoustic image data 15 and the image data 13 may be registered with each other in space and time, for example using conventional image registration techniques, allowing the system 1 to simultaneously produce two different types of image. This is advantageous in many fields, for example as a real time system for dynamic diagnostics and monitoring.

Similarly the system 1 might be integrated with an ultrasound treatment system, allowing monitoring of state of the object 2 during treatment.

Some examples of the system 1 applied to different applications in the field of medical imaging wherein the object 2 is human tissue are shown in FIGS. 7 to 9. In each case, the transmitter antenna 6 and receiver antenna 8 are replaced by a common antenna 16 connected to the radio frequency source 7 and the signal processing apparatus 9 via a directional coupler 17 that provides separation of the transmitted and received signals.

FIG. 7 illustrates the system 1 applied to mammography in which the object 2 is a breast. The acoustic transducer apparatus 4 and common antenna 16 are arranged on opposite sides of the breast, preferably with a matching medium between the breast and the acoustic transducer apparatus 4, for example oil, matching gel or a flexible membrane. The acoustic transducer apparatus 4 produces a narrow beam of acoustic vibration localized in two or three dimensions. The acoustic transducer apparatus 4 and common antenna 16 are rotated together as shown by the arrows A to obtain information from different directions that may be combined to derive a two dimensional image slice. Plural such image slices may be obtained by moving the acoustic transducer apparatus 4 and common antenna 16 up and down as shown by the arrows B.

FIG. 8 illustrates the system 1 applied as a full-body scanner in which the object 2 is the body of a human subject. The system 1 includes a bed 50 that comprises a flexible membrane 51 supported across the top of a bath 52 of containing matching medium 53. The subject lies on the flexible membrane 51 below the level of the matching medium 53. The acoustic transducer apparatus 4 and common antenna 16 are supported opposite one another on a rotatable gantry 54 that extends around the bath 52 so that the acoustic transducer apparatus 4 and common antenna 16 are on opposite sides of the subject. Rotation of the gantry 54 as shown by the arrows C allows information to be obtained from different directions that may be combined to derive a two dimensional image slice. Plural such image slices may be obtained by moving the gantry 54 as shown by the arrows B.

FIG. 9 illustrates the system 1 applied implementing the acoustic transducer apparatus 4 as a conventional hand-held apparatus of the type used for scanning a subject, for example during pregnancy. In this case, the common antenna 16 is simply arranged beneath the subject, for example beneath a bed on which the subject lies, and the acoustic transducer apparatus 4 is used in a conventional manner to simultaneously obtain an image in accordance with the present invention and a conventional acoustic image.

The invention claimed is:

1. A method comprising:
   applying to an object acoustic vibration localized in two or three dimensions in a plurality of regions in the object simultaneously but with different frequencies in each region;
   simultaneously illuminating the object with an illuminating electromagnetic wave that has a frequency in a range extending down from 30 THz, the vibration direction of the acoustic vibration having a component parallel to the propagation direction of the illuminating electromagnetic wave so that the acoustic vibration of the object in each of the plurality of regions generates a scattered electromagnetic wave including Doppler components shifted from the frequency of the illuminating electromagnetic wave by frequencies of the acoustic vibration and multiples thereof;

receiving the scattered electromagnetic wave generated in each of the plurality of regions, deriving from the received, scattered electromagnetic wave data representing at least one characteristic of the Doppler components in respect of each region; and storing the derived data in respect of each region as image data representing an image.

2. The method according to claim 1, wherein the object is human or animal tissue.

3. The method according to claim 1, wherein said range of the frequency of the illuminating electromagnetic wave extends down from 100 GHz.

4. The method according to claim 1, wherein said range of the frequency of the illuminating electromagnetic wave extends down to 100 MHz.

5. The method according to claim 1, wherein the acoustic vibration has a frequency in the range from 10 MHz to 1 GHz.

6. The method according to claim 1, wherein the vibration direction of the acoustic vibration and the propagation direction of the illuminating electromagnetic wave are parallel.

7. The method according to claim 1, wherein the scattered electromagnetic wave is received along a line parallel or antiparallel to the propagation direction of the illuminating electromagnetic wave.

8. The method according to claim 1, wherein at least one characteristic of the Doppler components includes at least one of an amplitude or a phase of one or more of the Doppler components.

9. The method according to claim 1, wherein the step of deriving at least one characteristic of the Doppler components comprises frequency-modulation demodulating the Doppler components from the component of the scattered electromagnetic wave of the same frequency as the illuminating electromagnetic wave.

10. The method according to claim 1, wherein the acoustic vibration applied to the object is localized in three dimensions in the plurality of regions in the object, being applied as pulses of different frequencies each localized in space in a first and second dimension in different regions and localized in a third dimension in different regions at different times as it propagates.

11. The method according to claim 1, wherein the acoustic vibration applied to the object is localized in three dimensions in the plurality of regions in the object, being applied as a plurality of simultaneous propagating beams of different frequencies localized in space in a first and second dimension in different regions and localized in a third dimension in different regions at different times as the beams propagate.

12. The method according to claim 1, wherein the electromagnetic wave has a radio frequency.

13. The method according to claim 1, wherein the step of applying to the object acoustic vibration localized in two or three dimensions in a plurality of regions in the object simultaneously but with different frequencies in each region further comprises scanning the plurality of regions across the object.

14. A system comprising:

an acoustic transducer apparatus including a drive circuit driving an array of transducers arranged to apply to an object acoustic vibration localized in two or three dimensions in a plurality of regions in the object simultaneously but with different frequencies in each region;

a transmitter arrangement including a transmitter antenna and a radio frequency source arranged to illuminate the object with an illuminating electromagnetic wave having a frequency in a range extending down from 30 THz simultaneously with the application of acoustic vibration, the vibration direction of the acoustic vibration having a component parallel to the propagation direction of the illuminating electromagnetic wave so that the acoustic vibration of the object in each of the plurality of regions generates a scattered electromagnetic wave including Doppler components shifted from the frequency of the illuminating electromagnetic wave by frequencies of the acoustic vibration and multiples thereof;

a receiver arrangement including a receiver antenna arranged to receive the scattered electromagnetic wave generated in each of the plurality of regions;

a signal processing apparatus arranged to derive, from the received scattered electromagnetic wave generated in respect of each region, data representing at least one characteristic of the Doppler components in respect of each region and arranged to store the derived data in respect of each region as image data representing and image.

15. The system according to claim 14, wherein said range of the frequency of the illuminating electromagnetic wave extends down from 100 GHz.

16. The system according to claim 14, wherein said range of the frequency of the illuminating electromagnetic wave extends down to 100 MHz.

17. The system according to claim 14, wherein the acoustic vibration has a frequency in the range from 10 MHz to 1 GHz.

18. The system according to claim 14, wherein the array of transducer and the transmitter antenna are positioned relative to each other such that the vibration direction of the acoustic vibration and the propagation direction of the illuminating electromagnetic wave are parallel.

19. The system according to claim 14, wherein the receiver arrangement is arranged to receive the scattered electromagnetic wave along a line parallel or antiparallel to the propagation directions of the illuminating electromagnetic wave.

20. The system according to claim 14, wherein at least one characteristic of the Doppler components includes at least one of the amplitude and phase of one or more of the Doppler components.

21. A system according to claim 14, wherein the signal processing apparatus includes a frequency-modulation demodulator arranged to demodulate the Doppler components from the component of the scattered electromagnetic wave of the same frequency as the illuminating electromagnetic wave.

22. The system according to claim 14, wherein the drive circuit and array of transducers are arranged to apply the acoustic vibration localized in three dimensions in the plurality of regions in the object, being arranged to apply the acoustic vibration as pulses of different frequencies each localized in space in first and second dimensions in different regions and localized in a third dimension in different regions at different times as the acoustic vibration propagates.

23. The system according to claim 14, wherein the drive circuit and array of transducers are arranged to apply the acoustic vibration localized in three dimensions in the plurality of regions in the object, the acoustic transducer apparatus being arranged to apply the acoustic vibration as a plurality of propagating beams of different frequencies localized in space in first and second dimensions in different regions and localized in a third dimension in different regions at different times as the beams propagate.

24. A system comprising:

an acoustic transducer apparatus including a drive circuit driving an array of transducers arranged to apply to an object acoustic vibration localized in two or three dimensions in a plurality of regions in the object simultaneously but with different frequencies in each region;

a transmitter arrangement including a common antenna and a radio frequency source arranged to illuminate the object with an illuminating electromagnetic wave having a frequency in a range extending down from 30 THz simultaneously with the application of acoustic vibration, the vibration direction of the acoustic vibration having a component parallel to the propagation direction of the illuminating electromagnetic wave so that the acoustic vibration of the object in each of the plurality of regions generates a scattered electromagnetic wave including Doppler components shifted from the frequency of the illuminating electromagnetic wave by frequencies of the acoustic vibration and multiples thereof, the common antenna arranged to receive the scattered electromagnetic wave generated in each of the plurality of regions;

a signal processing apparatus arranged to derive, from the received scattered electromagnetic wave generated in respect of each region, data representing at least one characteristic of the Doppler components in respect of each region and arranged to store the derived data in respect of each region as image data representing an image.

25. The system according to claim 24, wherein said range of the frequency of the illuminating electromagnetic wave extends down from 100 GHz.

26. The system according to claim 24, wherein said range of the frequency of the illuminating electromagnetic wave extends down to 100 MHz.

27. The system according to claim 24, wherein the acoustic vibration has a frequency in the range from 10 MHz to 1 GHz.

28. The system according to claim 24, wherein the array of transducers and the common antenna are positioned relative to each other such that the vibration direction of the acoustic vibration and the propagation direction of the illuminating electromagnetic wave are parallel.

29. The system according to claim 24, wherein at least one characteristic of the Doppler components includes at least one of the amplitude and phase of one or more of the Doppler components.

30. A system according to claim 24, wherein the signal processing apparatus includes a frequency-modulation demodulator arranged to demodulate the Doppler components from the component of the scattered electromagnetic wave of the same frequency as the illuminating electromagnetic wave.

31. The system according to claim 24, wherein the drive circuit and array of transducers are arranged to apply the acoustic vibration localized in three dimensions in the plurality of regions in the object, being arranged to apply the acoustic vibration as pulses of different frequencies each localized in space in first and second dimensions in different regions and localized in a third dimension in different regions at different times as the acoustic vibration propagates.

32. The system according to claim 24, wherein the drive circuit and array of transducers are arranged to apply the acoustic vibration localized in three dimensions in the plurality of regions in the object, the acoustic transducer apparatus being arranged to apply the acoustic vibration as a plurality of propagating beams of different frequencies localized in space in first and second dimensions in different regions and localized in a third dimension in different regions at different times as the beams propagate.

* * * * *